United States Patent [19]

McCoy et al.

[11] 4,038,376

[45] July 26, 1977

[54] PROCESS FOR THE RECOVERY OF SELENIUM FROM URETHANES CONTAINING SELENIUM OR COMPOUNDS THEREOF

[75] Inventors: John J. McCoy, Media; John G. Zajacek, Devon, both of Pa.

[73] Assignee: Atlantic Richfield Company, Los Angeles, Calif.

[21] Appl. No.: 603,998

[22] Filed: Aug. 12, 1975

[51] Int. Cl.² .................... C01B 19/00; C01B 25/14
[52] U.S. Cl. .................................................. 423/510
[58] Field of Search .................. 260/471 C; 423/510, 423/508, 509; 208/253, 251 R

[56] References Cited

U.S. PATENT DOCUMENTS

| | | | |
|---|---|---|---|
| 2,778,779 | 1/1957 | Donaldson | 208/253 |
| 3,387,928 | 6/1968 | Doumas | 423/509 |
| 3,546,103 | 12/1970 | Hamner et al. | 208/253 |
| 3,577,216 | 5/1971 | Weiss et al. | 423/509 |
| 3,933,624 | 1/1976 | Myers | 208/253 |
| 3,954,603 | 5/1976 | Curtin | 208/253 |

FOREIGN PATENT DOCUMENTS

| | | | |
|---|---|---|---|
| 622,101 | 6/1961 | Canada | 423/510 |
| 521,732 | 2/1956 | Canada | 423/510 |
| 661,882 | 11/1951 | United Kingdom | 423/510 |

*Primary Examiner*—O. R. Vertiz
*Assistant Examiner*—Eugene T. Wheelock
*Attorney, Agent, or Firm*—Delbert E. McCaslin

[57] ABSTRACT

A process for the recovery of selenium from a urethane solution containing selenium compounds which may be in the form of metallic selenium, inorganic selenium and/or organoselenium compounds which comprises contacting the selenium-containing urethane solution at suitable temperatures with a supported metal or a mixture of metals and/or metal oxide compounds, said metal selectively chosen from Group B metals, i.e., Group IB through VIIIB, metals of the Periodic Table and particularly supported copper and mixtures of copper and other metal oxide compounds of said group.

9 Claims, No Drawings

PROCESS FOR THE RECOVERY OF SELENIUM FROM URETHANES CONTAINING SELENIUM OR COMPOUNDS THEREOF

BACKGROUND OF THE INVENTION

In U.S. Pat. No. 3,895,054 there is disclosed a process for the manufacture of urethanes (carbamic acid esters) by reacting an organic compound containing at least one hydroxyl group with carbon monoxide and a nitrogenous organic compound at elevated temperature and pressure in the presence of a selenium catalyst and a base and/or water.

The present invention is directed to an effective method of recovering selenium from urethane solutions produced, for example, by the above described process and containing selenium which may be in the form of metallic selenium, inorganic selenium compounds or organoselenium compounds. Because of the high reactivity of selenium, when used as a catalyst as in the above reaction its combination with organic compounds very frequently results in the formation of organoselenium compounds which remain in solution with the urethane product. In such reaction, a portion of the selenium catalyst such as metallic selenium per se or selenium dioxide, selenium disulfide, selenium oxychloride, etc. is converted to one or more organoselenium compounds which may be classified generally as selenols, selenides, benzoselenazoles, esters of selenocarbonic acid, selenic acid and selenious acid, selenones and the like. The type and number of organoselenium compounds which may be formed in a function of the reaction conditions used to produce the urethanes such as time, temperature, pressure and solvent.

Because of the cost and toxicity of selenium, it is essential that as much of the selenium be recovered from the urethane reaction product as is possible and from the organoselenium compounds in a form suitable for reuse as a catalyst.

A number of prior art processes have been proposed for the recovery of selenium from various organic reaction products or for the deselenation of organoselenium compounds. However, such prior art processes are generally narrow in scope and application and have proven to be of little or no value to the recovery of selenium from urethane solutions containing same. In addition, such processes do not provide for recovery of the metallic selenium for reuse.

U.S. Pat. No. 3,048,604 discloses a deselenation of dehydrosteroids containing selenium by reaction of the contained selenium compound with copper powder at temperatures of from 100° to 300° C.

In an article by H. Hauptmann and W. F. Walter, Journal of the American Chemical Society, Vol. 77, pp. 4929–4930, Sept. 20, 1955, the action of Raney Nickel on organoselenium compounds to effect deselenization is described. A large excess of the Raney Nickel is necessary accompanied by long reaction times resulting in partial deselenization.

U.S. Pat. No. 3,084,994 discloses a method for the recovery of selenium from a gas containing selenium together with aldehydes and nitriles using water sprays to collect the selenium and atomizing the seleniumcontaining water in molecular oxygen-containing gas in contact with an oxide of copper, iron or nickel at 500° C. to convert the selenium in the water solution to selenium dioxide.

U.S. Pat. No. 3,577,216 discloses a process for the recovery of selenium IV used as a catalyst in the oxidative production of carboxylic acids by adding to the reaction products magnesium, zinc, aluminum, alkali and alkaline earth metal hydroxides, oxides, carbonates, bicarbonates and salts of the metals to precipitate metal selenite and reacting the metal selenite with a strong inorganic acid to obtain one of selenious acid and anhydride.

SUMMARY OF THE INVENTION

Thus the invention relates to a process for the recovery of selenium from organic solutions containing selenium or compounds thereof. More specifically, the present invention concerns a process for the recovery of selenium from an effluent solution obtained from the selenium catalyzed conversion of an organic nitrocompound to produce a urethane as described for example in the aforementioned Pat. No. 3,895,054 and incorporated herein by reference. The urethane products produced by such process, which may contain one or more organoselenium compounds as well as metallic selenium and/or inorganic selenium compounds, is contacted with a supported metal or a mixture of metals and/or metal oxides, which mixtures may also be supported, in order to retain and subsequently remove selenium without affecting the urethane product. The selenium retained by the supported metal or mixture of metals and/or metal oxides is then recovered in a form suitable for recycle and reuse as a catalyst upon, for example, by reaction with a suitable oxidant such as air at an elevated temperature and the selenium free supported metal or mixture of metals and/or metal oxides regenerated in a reducing atmosphere to render it suitable for reuse in the selenium removal step.

It is an object of this invention therefore to provide a process for the recovery of valuable selenium from selenium-containing urethane solutions and the ultimate purification of the urethane.

It is another object of this invention to provide a process for the recovery of selenium in a form suitable for recycle and reuse as a catalyst for the synthesis of urethanes from an organic compound containing at least one hydroxyl group with carbon monoxide and a nitrogenous organic compound.

It is a further object of this invention to recover the contained selenium values from urethane solutions utilizing a supported metal or a mixture of metals and/or metal oxide compounds to retain the selenium and to separate the selenium from and regenerate the supported metals or mixture of the metals and/or metal oxides in a reducing atmosphere suitable for recycle and reuse in the selenium removal process.

These and other objects and advantages of this invention will become apparent from the description of the invention which follows and from the claims.

DESCRIPTION OF THE INVENTION

In accordance with the present invention, a urethane solution containing selenium or compounds thereof, as, for example, a urethane solutions obtained by reacting an organic compound containing at least one hydroxyl group with carbon monoxide and an organic nitrogenous compound containing at least one non-cyclic group, in which a nitrogen atom is directly attached to a single carbon atom and is also attached through a double bond to an oxygen or nitrogen atom, at elevated temperatures and pressures in the presence of a metallic selenium or selenium compound catalyst and a base and/or water, is subjected to a treatment with a selected supported metal or a mixture of metals or a mixture of metals and a metal oxide selected from Group IB through VIIIB metals of the Periodic Table of Elements to retain and remove the selenium or compounds thereof from the solution to provide an essentially selenium free urethane solution and to recover the valuable selenium.

The selenium-containing urethane solutions may be contacted with the supported metal or mixture of metals or metal oxides by batch, semi-continuous or continuous process methods, for example, by adding the supported metal or mixture to the impure urethane solution and thereafter separating the supported metal or mixture from the urethane by any suitable means, such as filtering, or the selenium-containing solution may be passed through a heated bed or column of the supported metal or mixture and the essentially selenium free effluent urethane recovered leaving the retained selenium for further processing. Continuous or semi-continuous methods are preferred since there is no need to physically separate from the urethane.

Suitable metals for use in the process of the invention are selected from the Group B metals, i.e., Groups IB through VIIIB of the Periodic Chart of the Elements and particularly suitable metals are those selected from Groups, IB, IIB, VIB and VIIIB such as for example, nickel, copper, silver, zinc, chromium, cadmium, palladium and cobalt, with copper being most preferred. The metals may be used either individually on a support or as mixtures of metals and/or metal oxide or oxides in various combinations in both supported and unsupported states. When unsupported, the mixture of metals and/or metal oxide are most conveniently used as powder granules. When in a supported state a wide range of supports can be used, for example, silica, alumina, mixtures of silica and alumina, clay, keiselguhr, carbon and molecular sieve zeolites. When the metal is initially present as copper, cobalt, nickel, iron, palladium and platinum oxide it is preferable to pretreat with a reducing gas in order to essentially reduce to the metal. Such pretreatment or reduction can be most conveniently accomplished with hydrogen although other reducing gases such as CO can be used. Actual reduction procedures are well known in the art and while they may vary depending on the metal are generally carried out at a temperature of 80°–450° C. with a hydrogen pressure of 0.01–10 atmospheres.

Examples of metals or metal oxides suitable for selenium removal are copper on alumina, cobalt oxide on alumina, palladium on alumina, nickel oxide on alumina, copper oxide on alumina, mixtures of copper oxide and zinc oxide; copper oxide and copper chromite; copper oxide, cadmium oxide and chromium oxide. Particularly suitable formulations contain copper or mixtures of copper with other metals with the preferred formulation being $CuO/Al_2O_3$, $CuO/ZnO$ and $CuO/Cu Cr_2O_4$. Many such formulations are commerically available such as the Girdler Chemical Inc. G-66B and G-13 hydrogenation or dehydrogenation catalysts.

Among the criteria used to judge a good metal, metal oxide or supported metal system for selenium removal by the process of the invention are for example that it 1) maintain a high level of selenium removal while the selenium loading is increasing as measured by the weight ratio of available metal to reacted selenium and 2) that it not decompose any desired urethane reaction products in the selenium-containing solution.

The selenium removal reaction is generally conducted in the liquid phase. A single solvent or a mixture of solvents may also be used. Often the reaction solution from the selenium catalyzed reaction, i.e., the reactor effluent obtained from the selenium catalyzed conversion of an aromatic nitrocompound to a urethane, can be contacted directly with the support metal or mixture of metals and/or metal oxide or oxides. Alternatively the solvent present in the effluent urethane may be removed and replaced with another solvent. Suitable solvents and cosolvents include amines, alcohols, hydrocarbons, ethers, ketones, and glycol ethers. It is preferred to choose a solvent which is inert at the reaction conditions used and in which the organic components have good solubility. Particularly suitable solvents are the hydrocarbons such as benzene, toluene, xylene, trimethylbenzene, and tetralin or tetrahydrofuran.

The process of the invention is generally carried out at temperatures in the range of from about 25° to 250° C. and preferably at temperatures in the range of from about 75° to 150° C. The process temperature generally is dependent on the type of selenium compounds to be reacted and removed as well as the thermal stability of the product urethane.

Contact time of the selenium-containing urethane solution with the metal in the specific form utilized may vary within a range of from one minute to several hours depending upon the type of selenium compound to be reacted and removed and the temperature used. Generally, the range of contact times will be between 5 minutes and one hour, although longer or shorter contact times may be used.

Once the selenium removal from the urethane has been accomplished the selenium retained by the metal or mixtures can be recovered in a catalytically useful form. This recovery can be carried out in a number of ways. One method is to heat the form of the metal utilized to 250° to 750° C. in an inert gas stream and collect the volatilized metallic selenium. In addition, the selenium can be recoverd from the form of the metal used by employing an oxidizing agent.

A particularly suitable oxidant for the recovery of the selenium from the form of the metal used in the process of this invention is air or oxygen, which may, if desired, be diluted with nitrogen or steam. Selenium is converted to selenium dioxide which may easily be recovered from the effluent reactor stream by cooling the gas stream from the reactor to below the sublimation point of selenium dioxide (approx. 300° C.) to collect the $SeO_2$ or by passing the gas through a water or alcohol scrubber to dissolve the $SeO_2$ therein and recovering the $SeO_2$ by evaporating the water or alcohol. Suitable temperatures for the recovery of selenium from the form of the metal using air or oxygen are generally between about 250° to 800° C. with a preferred range of from about 400° to 650° C. The contact time of the oxygen containing gas stream with the metal may vary from 0.1 second to one hour with a preferred range of from one second to 30 minutes. The pressure of the oxygen containing gas stream may vary from between atmospheric and 50 atmospheres with the preferred pressure range being between about 1 atmosphere and 20 atmospheres.

After the selenium has been removed and recovered from the form of the metal utilized, the form of metal, i.e., supported metal, mixture of metals and/or metal oxide or oxides, may be regenerated in a reducing atmosphere to render the form of the metal suitable for reuse in the process for the removal of selenium from urethanes. The regeneration/reduction of the form of the metal may be carried out with hydrogen at a pressure of from 0.01–10 atmospheres and at temperatures of from 80° to 450° C. in suitable apparatus.

The following Examples are provided to illustrate the invention in accordance with the principles of this invention but are not to be construed as limiting the invention in any way except as indicated by the appended claims.

EXAMPLE I

The urethane solutions used in the following runs were obtained by taking the effluent from a metallic selenium catalyzed conversion of 2,4-dinitrotoluene to the corresponding diurethane which contained a mixture of metallic selenium and various organoselenium compounds not identified and evaporating to dryness. The residue was then dissolved in an approximately 1/1 (Vol/Vol) solution of equal parts tetrahydrofuran and trimethylbenzene. The resulting solution generally contained 5.0–8.0 weight per cent diurethane and 0.1–0.3 weight percent selenium as organoselenium compounds. The solutions were fed dropwise to a "Vycor" glass reactor tube from a syringe driven by a pump at a rate of 20–25 cc/hr. The reactor tube heated by a furnace, was packed with 10 cc. of the various forms of the metal except as noted, sized 20/40 mesh, except as noted, which has been previously reduced with hydrogen. After completion of the reaction the catalyst was washed thoroughly with tetrahydrofuran and the washings and effluent solution analyzed for selenium and diurethane. The results are shown in Table I.

TABLE II

| Time, hrs. | 1 | 2 | 3 | 4 | 5 | 6 | 7 | 8 |
|---|---|---|---|---|---|---|---|---|
| Wt. % Se Removed | 97.8 | 97.4 | 98.0 | 98.1 | 98.0 | 94.5 | 87.4 | 80.0 |

EXAMPLE III (Comparative)

The following example illustrates the use of the process described in U.S. Pat. No. 3,048,604 as applied to a diurethane reaction solution.

A portion of a reaction solution obtained from the selenium catalyzed conversion of 2,4-dinitrotoluene to the corresponding diethyl urethane was evaporated to dryness. The residue was dissolved in 50 ml. of diethyleneglycol monoethyl ether to give a solution containing a total of 0.131 g. of selenium and 8.1 g. of the urethane. The solution was refluxed with 1.0 g. copper powder for one-half hour, cooled and filtered. The solid on the filter was washed with acetone and the filtrate and wash combined. Analyses of the solution showed that 33.6 percent of the selenium was removed accompanied by a 41.8 percent loss of the diurethane.

EXAMPLE IV

A solution containing a complex mixture of unidentified organoselenium compounds was obtained from a selenium metal catalyzed conversion of 2,4-dinitrotoluene to the corresponding diurethane as described in U.S. Pat. No. 3,895,054. This reaction solution was first treated by bubbling air through the solution to precipitate and essentially remove by filtration the contained metallic selenium. The solution was then diluted with trimethylbenzene to give a solution with an organoselenium concentration of 0.20 percent by weight and a diurethane concentration of 8.69 percent by

TABLE I

| Run No. | Form of Metal | Wt. g. | Temp. ° C. | Se Chg'd. gm. | % Se Reacted | % Urethane Rec'd. |
|---|---|---|---|---|---|---|
| 1 | 32.5% CuO – 67.2% ZnO | 12.08 | 100 | 0.214 | 68.8 | 100 |
| 2 | 12.5% CuO/Al$_2$O$_3$ | 12.04 | 100 | 0.217 | 38.6 | 100 |
| 3 | 20% CuO, 28.5% CdO, 46.7% Cr$_2$O$_3$ | 15.41 | 100 | 0.185 | 52.7 | 100 |
| 4 | 79% CuO/Al$_2$O$_3$ | 14.5 | 100 | 0.058 | 50.2 | 96.6 |
| 5 | 10% CoO/Al$_2$O$_3$ | 13.41 | 100 | 0.064 | 11.0 | 93.0 |
| 6 | 52.5% CuO – 37.9% Cr$_2$O$_3$ | 14.7 | 100 | 0.116 | 71.0 | 100 |
| 7 | 4% Ag/Al$_2$O$_3$[1] | 23.3 | 100 | 0.204 | 9.0 | — |
| 8 | 75% ZnO/Al$_2$O$_3$[1] | 32.3 | 100 | 0.105 | 33.0 | 95 |
| 9 | 22% CuO, 18% Cr$_2$O$_{3/Al_2}$O$_3$[1] | 28.48 | 100 | 0.224 | 53.0 | 94 |
| 10 | Cu Metal (40–60 mesh granules) | 52.6 | 100 | 0.144 | 3.0 | — |
| 11 | 15% CuO/γ – Al$_2$O$_3$ | 10.45 | 100 | 0.064 | 82.8 | 62.1 |
| 12 | 12.5% CuO/α – Al$_2$O$_3$ | 12.22 | 100 | 0.12 | 55.4 | 100 |
| 13 | 32.5% CuO – 67.2% ZnO | 12.86 | 125 | 0.102 | 80.4 | 98.1 |
| 14 | 32.5% CuO – 67.2% ZnO | 12.82 | 150 | 0.176 | 76.1 | 75.1 |

[1]Reactor packed with 20 cc.

EXAMPLE II

A diurethane reaction solution obtained as in Example I in trimethylbenzene containing 0.20 weight percent selenium as organoselenium compounds was pumped upflow through a reactor packed with 10 cc., 12.8 g. of 32.5 percent by weight CuO and 67.2 percent by weight ZnO which was reduced with hydrogen. The catalyst bed was held at 100° C. while the liquid flow rate was 25–30 cc./hr. Samples of the effluent solution were taken each hour and analyzed for selenium. The overall urethane recovery was 95.3 percent. The results are shown in Table II.

weight.

An 18 millimeter O.D. Vycor glass reaction tube was packed with 12.8 grams of 32.5 percent by weight CuO/67.2 percent by weight ZnO catalyst which had been sized through 20 mesh on 40 mesh (U.S. Standard Sieve). The catalyst was then reduced with 2 mole percent hydrogen in nitrogen diluent at 250°–300° C.

The reactor was cooled to 100° C. and the selenium containing solution was pumped upflow at a rate of 25 milliliters per hour through the reactor. Samples of the reactor effluent were taken hourly and analyzed for selenium and diurethane with the following results:

| Reaction Time, hours Wt. % Se Adsorbed | | | | | | | |
|---|---|---|---|---|---|---|---|
| Hrs. 1 | 2 | 3 | 4 | 5 | 6 | 7 | 8 |
| 97.8 | 97.4 | 98.0 | 98.1 | 98.0 | 94.5 | 87.4 | 80.0 |

The overall diurethane recovery was 95.3 percent.

EXAMPLE V

A CuO/ZnO mixture was prepared by dissolving 277.8 grams $Cu(NO_3)_2 \cdot 3H_2O$ and 647.6 grams $Zn(NO_3)_2 \cdot 6H_2O$ into 10,000 milliliters of 2 percent nitric acid. To this solution was added over a five-hour period five liters of a solution containing 846.9 grams $Na_2CO_3 \cdot H_2O$. The resulting mixture was allowed to stir at room temperature for sixty hours. The solution was then filtered and the solid washed eight times using 10,000 milliliters water for each wash.

The solid cake was dried at 120° C., broken and sized through 20 mesh on 40 mesh (U.S. Standard Seive). Analysis of the solid showed a composition containing 33.4 per cent by weight CuO and 66.5 percent by weight ZnO, on a water free basis.

A total of 16.5 grams of the CuO/ZnO mixture was charged to a Vycor glass reactor as described in Example IV and reduced with 2 mole percent hydrogen in a nitrogen diluent at 250°-300° C.

A solution containing a complex mixture of unidentified organo-selenium compounds was obtained from a selenium metal catalyzed conversion of 2,4-dinitrotoluene to the corresponding diurethane as described in U.S. Pat. No. 3,895,054. This reaction solution was treated as in Example IV above to essentially remove metallic selenium and was then evaporated with continual addition of trimethylbenzene until all the original reaction solvent consisting of ethanol, pyridine, and triethylamine was replaced with trimethylbenzene. The solution was then pumped upflow through the reactor at a rate of 25 milliliters per hour at a reactor temperature of 130° C. Samples of the reactor effluent were taken hourly and analyzed for selenium. After five hours of operation the reaction was discontinued, the reactor cooled and washed with tetrahydrofuran. The bed was then dried in a stream of nitrogen at 100° C. and the selenium recovery phase of the cycle carried out as follows.

A flow of nitrogen at 100 milliliters/minute and air at 30 milliliters/minute was passed through the reactor at 100° C. When oxidation of the copper was complete, the reactor temperature was raised to 400° C. with a nitrogen flow of 100 milliliters/minute and an air flow of 10 milliliters minute. The air flow was gradually increased as the adsorbed organic material underwent combustion. When combustion was complete, the reactor temperature was increased to 450°-550° C. and the air flow was increased to 300 milliliters/minute. Selenium dioxide along with a small amount of metallic selenium was evolved and was collected in a series of cooled tubes and gas scrubbers containing nitric acid which were connected in series to the outlet of the reactor. When the reaction was discontinued after one to three hours, the contents of the traps were analyzed and the total amount of selenium determined. The reactor was cooled to 250°-300° C. and the CuO/ZnO mixture reduced with 2 mole percent hydrogen in a nitrogen diluent as described above and the next cycle was begun.

Table II below shows the results obtained by operating the above described CuO/ZnO charge through a total of five cycles, each cycle consisting of a reduction, selenium retention or adsorption and selenium recovery step.

TABLE III

| | | Se Retained | | | Se Recovery | | |
|---|---|---|---|---|---|---|---|
| Cycle | Feed Wt. % Se | Initial Wt. g. Se Retained | Final Wt. g. Se Retained | Wt. Se g. Retained this cycle | Temp. ° C. | Wt. Se g. Recovered | Wt. % Total Adsorbed Se Recovered |
| 1 | 0.14 | 0.00 | 0.137 | 0.137 | 450 | 0.014 | 10.5 |
| 2 | 0.235 | 0.123 | 0.302 | 0.180 | 450 | 0.028 | 9.1 |
| 3 | 0.235 | 0.275 | 0.435 | 0.160 | 500 | 0.304 | 69.4 |
| 4 | 0.153 | 0.131 | 0.225 | 0.094 | 500 | 0.109 | 47.9 |
| 5 | 0.153 | 0.116 | 0.234 | 0.118 | 500 | 0.076 | 32.0 |

EXAMPLE VI

In a similar set of experiments a copper chromite powder consisting of 51 percent CuO/47 percent $Cr_2O_3$ was pelletized and sized through 20 mesh on 40 mesh (U.S. Standard Sieve). A total of 15.2 grams of this material was charged to the Vycor reactor and a series of cycles carried out as described in Example V above with the results shown in Table IV below.

TABLE IV

| | | Se Retained | | | Se Recovery | | |
|---|---|---|---|---|---|---|---|
| Cycle | Feed Wt. % Se | Initial Wt. g. Se Retained | Final Wt. g. Se Retained | Wt. Se g. Retained this cycle | Temp. ° C. | Wt. Se g. Recovered | Wt. % Total Adsorbed Se Recovered |
| 1 | 0.134 | 0.00 | 0.116 | 0.116 | 550 | 0.06 | 51.7 |
| 2 | 0.138 | 0.056 | 0.165 | 0.109 | 550 | 0.125 | 75.6 |
| 3 | 0.138 | 0.040 | 0.131 | 0.091 | 550 | 0.067 | 51.2 |

EXAMPLE VII

A copper chromite mixture (20 cc., 26.42 g.) containing 51 weight percent CuO and 47 weight percent $Cr_2O_3$ was hydrogenated with hydrogen at 18 cc/min. at a temperature of 250°-300° C. A solution of soluble inorganic and organoselenium compounds in 1,2,4-triemethylbenzene containing diethyl toluene-2,4-dicarbanate and by-products was pumped through a heated pump through a Vycor reactor bed at a rate of 40 cc./hr. The solution contained 0.138 weight percent selenium, which was equivalent to 0.046 g. Se being fed through the reactor each hour. The catalyst bed was maintained at 100° C. during the first four hours of the run the effluents contained less than 2 mg. of selenium per hour. Between the 5th and 10th hour of operation the amount of Se in the effluent increased from 2 mg. to 15 mg. Results are tabulated in Table V below.

effectiveness of the supported metal and mixture of metals and/or metal oxides of the invention to remove

TABLE VII

| Run No. | Amt. and Form of Metal | Se Compound | Solvent | Temp. °C. | Se Chg'd gms. | % Se Removed |
|---|---|---|---|---|---|---|
| 1 | 79% CuO/Al$_2$O$_3$ (15.89 g.) | 2-Benzoselenazole | THF/xylene | 100 | 0.814 | 99.5 |
| 2 | Cu Powder (0.5 g.) | 2-Benzoselenazole | xylene | 136 | 0.50 | 5.0 |
| 3 | Cu Powder (0.5 g.) | diethyldiselenide | xylene | 136 | 0.36 | 11.0 |
| 4 | 79% CuO/Al$_2$O$_3$ (14.5 g.) | diphenyldiselenide | xylene | 100 | 0.827 | 91.7 |
| 5 | 12% CuO/Al$_2$O$_3$ (9.69 g.) | diphenyldiselenide | trimethylbenzene | 100 | 0.810 | 77.7 |
| 6 | 32.5% CuO, – 67.2% ZnO (12.16 g.) | diphenyldiselenide | trimethylbenzene | 100 | 0.810 | 98.2 |
| 7 | 10% CoO/Al$_2$O$_3$ 12.45 g.) | diphenyldiselenide | trimethylbenzene | 100 | 0.810 | 92.9 |
| 8 | 45% CuO, 45% CuCrO$_2$O$_4$, 10% Cr$_2$O$_3$ (15.2 g.) | diethyldiselenide | trimethylbenzene | 100 | 1.21 | 94.0 |

TABLE V

| Time, (hrs.) | g. Se in effluent | % Se removal during previous hour | Overall % Se removal from start of run |
|---|---|---|---|
| 1 | <0.001 | 99+ | 99+ |
| 2 | <0.001 | 99+ | 99+ |
| 3 | <0.002 | 98 | 98+ |
| 4 | <0.002 | 97 | 98 |
| 5 | 0.002 | 96 | 98 |
| 6 | 0.004 | 91 | 97 |
| 7 | 0.009 | 80 | 94 |
| 8 | 0.011 | 76 | 92 |
| 9 | 0.013 | 72 | 90 |
| 10 | 0.015 | 67 | 88 |

EXAMPLE VIII

A run was carried out according to the procedure of Example VII except that the feed solution contained 0.10 weight percent Se and the temperature of the reactor was 130° C. The input to the reactor contained 0.034 g. Se/hour and the mixture of metals contained 52.5 weight percent CuO and 37.9 weight percent Cr$_2$O$_3$. During yhe first five hours of operation the effluents contained less than 1 mg. Se per hour. During the 6th and 7th hour about 1 mg. Se was unreacted each hour, and during the 8th and 9th hours 3 and 5 mg. Se respectively came through unreacted. Results are tabulated in Table VI below.

TABLE VI

| Time (hrs.) | g. Se in effluent | % Se removal during previous hour | Overall % Se removal from start of run |
|---|---|---|---|
| 1 | 0 | 99+ | 99+ |
| 2 | 0 | 99+ | 99+ |
| 3 | 0 | 99+ | 99+ |
| 4 | 0 | 99+ | 99+ |
| 5 | 0 | 99+ | 99+ |
| 6 | 0.001 | 97 | 99+ |
| 7 | 0.001 | 97 | 99 |
| 8 | 0.003 | 91 | 98 |
| 9 | 0.005 | 85 | 97 |

EXAMPLE IX

A number of runs were made in accordance with the procedures of Example IV, utilizing various solvent diluted pure organoselenium compounds which may be encountered in the effluent urethane solutions from the selenium catalyzed reaction described in U.S. Pat. No. 3,895,054 and various forms of the reduced supported metals or mixtures of metals and metal oxides as well as unsupported copper powder. These runs the results of which are shown in Table VII below demonstrate the effectiveness of the supported metal and mixture of metals and/or metal oxides of the invention to remove the selenium compounds from solution and compared, for example, with metal powder.

We claim:

1. A process for the recovery of selenium or compounds thereof from selenium-containing urethane solutions derived from the selenium catalyzed reaction of an organic compound containing at least one hydroxyl group with carbon monoxide and a nitrogenous organic compound at elevated temperatures and pressures in the presence of a base and/or water, which comprises treating said urethane solution with a metal oxide at a temperature in the range of from about 25° to 250° C. to retain and remove said selenium or compounds thereof from said urethane solution, said metal oxide being selected from oxides of Group B metals of the Periodic Table of Elements, and recovering said selenium and the treated urethane solution.

2. A process according to claim 1 wherein the metal oxide with retained selenium or compounds thereof is subjected to treatment with air or oxygen at temperatures of from 250° to 800° C. and pressures of up to 50 atmospheres to convert the selenium to selenium dioxide, and recovering said selenium dioxide from said metal oxide for reuse in said selenium catalyzed reaction.

3. A process according to claim 2 wherein the treatment with air or oxygen is carried out at a temperature in the range of from about 400° to 650° C. and a pressure of from 1 to 20 atmospheres.

4. A process according to claim 1 wherein the metal oxide is copper oxide.

5. A process according to claim 1 wherein the temperature is in the range of from about 75° to 150° C.

6. A process according to claim 1 wherein the metal oxide is selected from the group consisting of cobalt oxide, copper oxide, nickel oxide, cadmium oxide, chromium oxide and zinc oxide.

7. A process according to claim 6 wherein the metal oxide is a mixture of copper oxide and zinc oxide, copper oxide and copper chromite or, copper oxide, cadmium oxide and chromium oxide.

8. A process according to claim 1 wherein an inert solvent or mixture of solvents is added to the selenium-containing urethane solution prior to said treatment.

9. A process according to claim 8 wherein the solvents are selected from the group consisting of benzene, toluene, xylene, tetrahydrofuran, trimethylbenzene and tetralin.

* * * * *